US012137881B2

(12) United States Patent
Saltzburg (10) Patent No.: US 12,137,881 B2
(45) Date of Patent: *Nov. 12, 2024

(54) MULTIFUNCTIONAL INTRAORAL IMAGING SYSTEM AND RELATED METHODS (71) Applicant: Harris Rand Saltzburg, Elizabeth, NJ (US)

(72) Inventor: Harris Rand Saltzburg, Elizabeth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/205,323

(22) Filed: Jun. 2, 2023

(65) Prior Publication Data
US 2023/0309811 A1    Oct. 5, 2023

Related U.S. Application Data (63) Continuation of application No. 17/876,516, filed as application No. PCT/US2022/018051 on Feb. 26, 2022, now Pat. No. 11,690,505.

(60) Provisional application No. 63/154,074, filed on Feb. 26, 2021.

(51) Int. Cl.
*A61C 3/00* (2006.01)
*A61B 1/00* (2006.01)
*A61B 1/04* (2006.01)
*A61B 1/247* (2006.01)

(52) U.S. Cl.
CPC .......... *A61B 1/247* (2013.01); *A61B 1/00016* (2013.01); *A61B 1/00048* (2013.01); *A61B 1/00108* (2013.01); *A61B 1/042* (2013.01); *A61B 2560/0443* (2013.01)

(58) Field of Classification Search
CPC . A61B 1/247; A61B 1/00016; A61B 1/00048; A61B 1/00108; A61B 1/042; A61B 2560/0443
See application file for complete search history.

(56) References Cited

U.S. PATENT DOCUMENTS

| 5,986,271 A | * | 11/1999 | Lazarev | ................. | A61B 1/043 250/461.1 |
| 8,087,932 B2 | * | 1/2012 | Liu | .......................... | A61C 7/00 382/128 |
| 8,200,073 B1 | * | 6/2012 | Nakamura | ......... | A61B 1/00193 348/66 |

(Continued)

*Primary Examiner* — Howard D Brown, Jr.
(74) *Attorney, Agent, or Firm* — Wiggin and Dana LLP (57) ABSTRACT The present disclosure relates to visualizing an operative field in the context of a dental operating theater, and more specifically, to a portable, modular, multifunctional intraoral imaging system to assist a practitioner in performing a medical or dental procedure in a confined space (e.g., intraoral cavity or mouth of a patient). The system may include an intraoral camera apparatus having a camera unit equipped with a wireless transmitter, and a viewscreen mounted to an articulated stand or dental delivery unit, wherein the camera wirelessly may transmit an image to a viewscreen located directly in front of a dental practitioner. The practitioner may look directly ahead at a high-definition screen to view the operative field. A dental practitioner may use the apparatus to perform micro-surgical procedures in a confined operative area with less-than-ideal visibility and access, without the present, though generally accepted, physical difficulties and limitations.

20 Claims, 6 Drawing Sheets

(56) References Cited

U.S. PATENT DOCUMENTS

| | | | | |
|---|---|---|---|---|
| 2002/0182575 | A1* | 12/2002 | Vannoye | G16H 70/20 |
| | | | | 434/263 |
| 2004/0007907 | A1* | 1/2004 | DiRe | A61G 15/12 |
| | | | | 297/217.3 |
| 2006/0252004 | A1* | 11/2006 | Donahoo | A61C 19/00 |
| | | | | 433/29 |
| 2008/0084965 | A1* | 4/2008 | Ohnona | A61B 6/548 |
| | | | | 707/999.107 |
| 2008/0090199 | A1* | 4/2008 | Noguchi | A61B 5/0066 |
| | | | | 433/29 |
| 2010/0112513 | A1* | 5/2010 | Frojdman | A61G 15/00 |
| | | | | 433/33 |
| 2013/0330684 | A1* | 12/2013 | Dillon | A61B 1/00042 |
| | | | | 433/29 |
| 2015/0350517 | A1* | 12/2015 | Duret | G02B 27/0176 |
| | | | | 348/66 |
| 2017/0000677 | A1* | 1/2017 | Prince | A61G 15/16 |

* cited by examiner

MULTIFUNCTIONAL INTRAORAL IMAGING SYSTEM AND RELATED METHODS

CROSS-REFERENCE TO RELATED APPLICATIONS

This application is a continuation of pending U.S. patent application Ser. No. 17/876,516 filed on Jul. 28, 2022, which claims the benefit of priority based on the U.S. national phase entry of PCT Application No. PCT/US2022/018051, filed Feb. 26, 2022, which itself claims the benefit of priority to U.S. Provisional Patent Application No. 63/154,074, filed Feb. 26, 2021. All of these prior applications are herein incorporated by reference in their entirety.

TECHNICAL FIELD

The present disclosure relates to systems, apparatuses, and related methods for visualizing an operative field in the context of a dental operating theater, and more specifically, to a portable, modular, multifunctional intraoral imaging system to assist a medical practitioner (e.g., surgeon, dentist, doctor, dental hygienist, etc.) in performing a medical or dental procedure (e.g., dental surgery, dental procedure etc.) in a confined space (e.g., intraoral cavity or mouth of a patient) to reduce or eliminate any contorting required by the medical practitioner's body during the imaging or during the procedure.

BACKGROUND

The conventional dental operating theater is arranged such that the patient is placed in a comfortable, fully reclining chair with articulating headrest while the dentist sits on a stool at the three-six-twelve o'clock position (if right-handed or, the opposite if left-handed). Throughout treatment, the patient remains recumbent as the dental professional seeks to visualize the operative field by either contorting themselves to achieve direct vision or through the manipulation of a dental hand mirror of approximately 25 mm diameter. The Dentist routinely utilizes a Dental Assistant, who sits on a specifically designed stool that allows arms to rest upon a padded bar, usually at the dentist's non-working side. The Dental Assistant's role is to provide adequate cheek/tongue retraction and water/saliva control.

Dentistry is a crippling profession that places unfathomable physical stress upon the cervical and lumbar spines and the pectoral and pelvic girdles of the dental professional. The difficulty relates to the contortions that the practitioner must adopt to adequately visualize the operative field, all while performing micro-surgical procedures that demand the utmost in hand-eye coordination, dexterity and physical stability, often for hours on end. During a decades-long career, musculo-skeletal pathology is inherent and practically unavoidable.

An otoscope is useful to illuminate an ear, and endoscope a body cavity such as mouth or rectum, a laparoscope the organs of the abdomen and a arthroscope joints between bones. However, there is not an illumination source for intraoral imaging that addresses the unique problems experienced by a dentist as described herein.

Therefore, a need exists to create a multifunctional intraoral imaging system that is portable, modular, and interactive to assist a medical practitioner (e.g., surgeon, dentist, doctor, dental hygienist, etc.) in performing a medical or dental procedure (e.g., dental surgery, dental procedure etc.) in a confined space (e.g., intraoral cavity or mouth of a patient) without contorting their body.

SUMMARY

To overcome and mitigate the deficiencies noted above with commercially available dental imaging devices, this disclosure presents an ergonomic solution that provides a dental practitioner with a superior range of vision without requiring the practitioner to contort themselves to properly visualize the operative field.

If an apparatus could be developed that would project an active image of the operative field to a high-resolution screen directly in front of the practitioner, then there would be no need for the individual to contort themselves to provide patient care. No hand mirror. No bending, twisting, torquing of the cervical- or lumbar-spine. Simple operation in a comfortable, ergonomically idealized environment would be possible.

The present disclosure describes embodiments of an apparatus to address the above-identified concerns. The embodiments described herein permit micro-surgical procedures in a confined operative area with less-than-ideal visibility and access, without the present, though generally accepted, physical difficulties and limitations.

Embodiments of the present disclosure relate to, among other things, systems, apparatuses, and related methods for visualizing an operative field in the context of a dental operating theater. More specifically, to portable, modular, multifunctional intraoral imaging systems configured to assist a medical practitioner (e.g., surgeon, dentist, doctor, dental hygienist, etc.) in performing one or more medical or dental procedure(s) (e.g., dental surgery, dental procedure etc.) in a confined space (e.g., intraoral cavity or mouth of a patient) without the practitioner contorting their body or otherwise inducing back and/or neck pain while conducting the procedure(s).

In one exemplary embodiment, the embodiment is a system. This exemplary system may include a moveable imaging and display system comprising a moveable base; an adjustable stand mounted to the base, wherein the stand includes three sections: a first section having an upper end and a lower end, wherein the lower end is mounted to the movable base; a second section having a curved upper end and a lower end, wherein the lower end of the second section is rotatably mounted to the upper end of the first section; and a third section having a distal end and a proximal end, wherein the proximal end of the third section is rotatably mounted to the upper end of the second section; a tray unit rotatably mounted by way of a laterally extending arm to the first section of the adjustable stand; a camera module mounted to the tray unit, wherein the camera module includes an articulating neck having a proximal end mounted to the tray unit and a distal end to which is mounted a camera unit; and a display holder rotatably mounted to the distal end of the third section of the adjustable base.

In another exemplary embodiment, the embodiment is a system. This exemplary system may include a moveable intraoral imaging and display system, comprising: a movable base having a top and a bottom, the base having a plurality of wheels attached to the bottom of the base; a power cable attached to a side of the base; an adjustable telescoping vertical stand attached to a top of the base, wherein the adjustable telescoping vertical stand includes: a first tube section attached to the top of the base; a second tube section attached to a top of the first tube section via a first rotatable collar; and a third tube section attached to a top of the second tube section via a second rotatable collar; a first curved tubular section attached to a top of the third tube section via a third rotatable collar; a second curved tubular section attached to a distal end of the first curved tubular section via a fourth rotatable collar; fourth tube section attached to a distal end of the second curved section via a fifth rotatable collar, wherein a display holder unit is mounted to a distal end of the fourth tube section; a transverse tube section attached to the second rotatable collar of the adjustable section; a tray unit attached to a distal end of the transverse tube section; a camera module attached to a distal end of the tray unit, wherein the camera module includes a base to which the tray unit is attached, an articulating neck to which the base is attached, and a camera unit to which the articulating neck is attached, wherein the articulating neck includes a bend-and-stay wire.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure. In the figures.

DETAILED DESCRIPTION

While the present disclosure is described herein with reference to illustrative embodiments for particular applications, it should be understood that embodiments of the present disclosure are not limited thereto. Other embodiments are possible, and modifications can be made to the described embodiments within the spirit and scope of the teachings herein, as they may be applied to the above-noted field of the present disclosure or to any additional fields in which such embodiments would be of significant utility. For example, embodiments described herein can be used with any good and/or service related to imaging in a medical procedure in order to reduce or remove stresses or painful, or otherwise uncomfortable contouring of a practitioner's body.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, patent documents, whitepapers, and technical papers referred to in this document or in the attached appendices are incorporated by reference in their entirety herein, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Embodiments of the present disclosure relate to, among other things, systems, apparatuses, and related methods for visualizing an operative field in the context of a dental operating theater. More specifically, to portable, modular, multifunctional intraoral imaging systems configured to assist a medical practitioner (e.g., surgeon, dentist, doctor, dental hygienist, etc.) in performing one or more medical or dental procedure(s) (e.g., dental surgery, dental procedure etc.) in a confined space (e.g., intraoral cavity or mouth of a patient) without the practitioner contorting their body or otherwise inducing back and/or neck pain while conducting the procedure(s).

The term "distal", as used herein, may refer to a section closer to a patient. The term "proximal", as used herein, may refer to a section closer to a practitioner (e.g., a dentist, a surgeon, or any other medical/dental professional).

In an exemplary embodiment, the present disclosure describes an active, portable, multifunctional intraoral imaging system 100 which, through alleviating physical difficulties encountered by the dental practitioner while working in a confined operative area with less-than-ideal visibility and access, represents a paradigm shift in the practice of dentistry. It can be appreciated by one of ordinary skill in the art that the benefits of this exemplary multifunctional intraoral imaging system may be used in non-dental procedures (e.g., by an oral maxillofacial surgeon, or other physician, or any other suitable medical practitioner).

Figure 1:
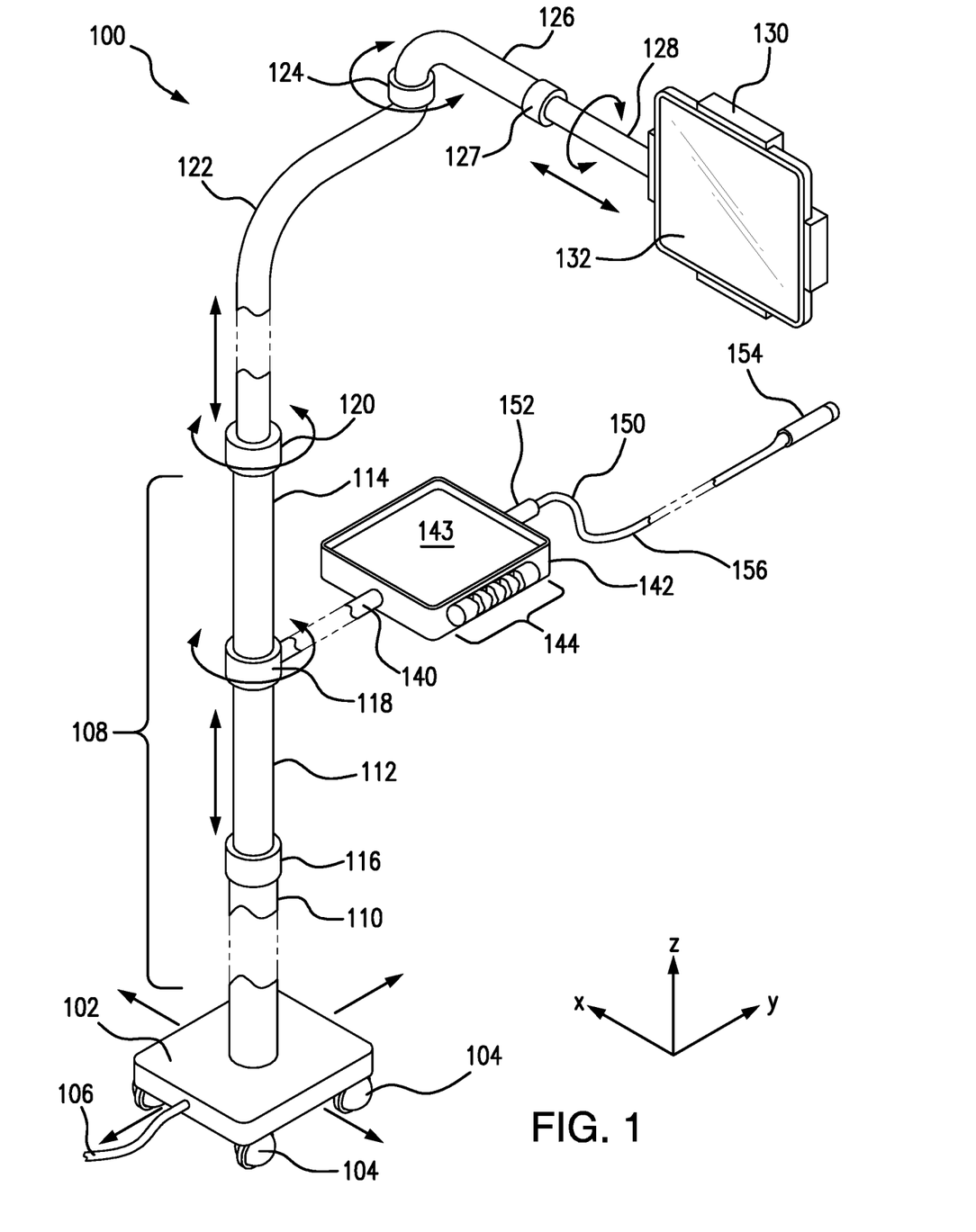
FIG. 1 illustrates a perspective view of a portable multifunctional intraoral imaging system, including a primary camera module and a rotatable display, in accordance with an exemplary embodiment of the present disclosure.

As will be explained in greater detail below, the multifunctional intraoral imaging system 100, as depicted in FIG. 1, may include a primary camera module having a camera capable of transmitting an image of the operative field to a screen directly in front of the practitioner (e.g., dentist, dental hygienist, or any other suitable medical practitioner). In an exemplary embodiment, in accordance with the present disclosure, the multifunctional intraoral imaging system 100 may be referred to "system 100". During use of the imaging system 100, the practitioner may look directly ahead at a high-definition 10- to 15-inch screen to view the operative field. By using this intraoral camera apparatus of the system 100, dental practitioners will no longer be dependent upon an intra-oral mirror or direct vision, both of which require the practitioner to twist into crippling contortions in order to treat their patients. The system 100 additionally frees up extra space in the operative area by implementing all connections via Bluetooth® communication, thereby removing the need for bulky wires, which reduces costs to the practitioner and the associated medical practice. Bluetooth® is a registered trademark of the Bluetooth Special Interest Group.

With detailed reference now to the Figures, FIG. 1 shows a perspective view of the portable multifunctional intraoral imaging system 100, including a primary camera module 150 and a rotatable display holder unit 130 (or an adjustable display screen holder or an adjustable clamping mechanism), in accordance with an exemplary embodiment of the present disclosure. The display holder unit 130 may be configured to secure a hi-definition flat panel screen (e.g., tablet) with on/off control and SD-slots, wireless internet and Bluetooth® capabilities, and permit display sizes ranging from 14-24 inches (diagonal). The imaging system 100 may include a base unit or a rolling stand unit 102, and may have four wheels 104 mounted to a bottom surface of the base unit 102, as shown, to permit the imaging system 100 to move about a X-Y axes plane. The base unit 102 of the imaging system 100 may be adapted to permit utilizing the imaging system 100 in both the right-handed and left-handed operatories (e.g., dental operatories).

In an exemplary embodiment, the base unit 102 may be a one-foot cast-metal square that incorporates four 2.5-inch, locking casters. In another embodiment, the rolling stand 102 may be comprised of a rolling or slidable base. In doing so, the imaging system 100 is portable and may be moved by a practitioner (e.g., dentist, doctor, surgeon, etc.) or by the practitioner's assistant (e.g., dental assistant, dental hygienist, physician assistant, etc.) between one operating/patient's room to another operating/patient's room. The imaging system 100 may be powered by a power cable 106, and may utilize a standard medical grade power cable to power the imaging system 100. The power cable 106 may be part of medical-grade power supplies that may have been specially designed to meet the IEC60601 medical equipment safety standard. IEC60601-rated power supplies must have effective and reliable isolation between the AC input to the power supply, the internal high voltage stages, and the DC output. In an exemplary embodiment, the imaging system 100 may be operated using a foot-operated controller that allows for hands-free operation of the system 100.

The imaging system 100 may also include an adjustable section 108 (e.g., a telescoping primary, height-adjustable, tube with a 90° L-bend connecting to a length-adjustable telescoping arm) of the imaging system 100 to permit a practitioner to adjust (e.g., increase or decrease) the height of the display holder unit 130 relative to the practitioner's eyes such that the practitioner may avoid having to look down or up by adjusting the height of the imaging system 100. The adjustable section 108 may be formed with sections 110, 112, and 114, as shown, and connected at rotatable collars 116, 118, and 120. The adjustable section may be configured and dimensioned to allow the imaging system to height adjust along a Z-axis, and rotate a lower arm 140, via rotatable collar 118, to rotate the lower arm 140 about the Z-axis. Attached to a top end of section 114, via rotatable collar 120, is L-shaped section 122, which may also be configured and dimensioned to be height adjustable along the Z-axis. The L-shaped section 122 (or curved section 122) may also be configured to rotate, via the rotatable collar 120, about the Z-axis. Extending from a top section of the L-shaped section 122, as shown, may be an upper arm 126. Similar to the lower arm 140, the upper arm 126 (or curved section 126) may be rotatably attached to L-shaped section 122, via a rotatable collar 124, to permit the upper arm 126 to rotate about the Z-axis. Extending yet further from upper arm 126, is the display unit arm 128, as shown. The display unit arm 128 may be rotatably connected to the upper arm 126 via a rotatable collar 127, such that the display unit arm 128 may rotate about the X-axis. A portable display 132 (e.g., computer tablet, or similar tablet PC) may be detachably mounted within a display holder 130 of the imaging system 100, as shown in FIG. 1. The portable display may be 14-24 inches in size diagonally. Examples of a display that may be suitable to work with the imaging system 100 include any smart tablet (PC or otherwise) with a touch screen display. The portable display 132 may be owned by the practitioner and/or by the practitioner's practice such that it may possess real-time, online network access, via a central server or a cloud computing service, to access one or more patient files (e.g., dental records, medical records, patient visit history, etc.). The display holder 130 may be rotatable about the X-axis via the rotatable collar 127, as described. Moreover, the display holder 130 may be configured and dimensioned such that the portable display 132 can be press-fit into the display holder 130 to secure or hold the display while the practitioner views the display during imaging and/or a procedure.

The primary tube of the adjustable section 108 of the imaging system 100 may include two height adjusters, as shown. In its collapsed state, the primary tube may be approximately 39 inches in height. The two rotatable collars 116 and 120 may be adjustment rings, may be sealed, and may be twist locks that may be loosened/tightened by hand. This may permit the extension of the base unit 102 by an additional 24 inches. An instrument tray 142, which may house a power junction, a Bluetooth® module and assorted software, may be disposed between the two sealed, twist-lock adjustment rings 116 and 120, may rotate 360° in the X-Y plane, and the rotatable collar 118 to which the tray 142 is attached may incorporate internal stop-clicks every 30° for a total of 12 stops.

The secondary length-adjustable tube (e.g., upper arm 126) may connect to the terminus of the 90° L-shaped section 122, by way of rotatable collar 124, and may rotate 360° in the Y-Z plane in its socket, incorporating internal stop-clicks every 30° for a total of 12 stops. When collapsed, the secondary length-adjustable tube (e.g., upper arm 126) is 18 inches in length. Rotatable collar 127 may be configured to also incorporate a sealed, twist-lock adjustment ring that permits a further 12-inch extension of the display unit arm 128 outward from the secondary length-adjustable tube (e.g., upper arm 126). With this extension, the rotatable collar 127 may be configured to allow for 360° rotation of the display holder 130 with internal stop-clicks every 30° for a total of 12 stops.

The display screen 132 of the imaging system 100 may be a HiDef Video Screen that may be attached via an adjustable, telescoping arm to the rolling stand unit 102 of the imaging system 100. A junction box within the tray 142 of the imaging system 100 may serve to connect the imaging system's 100 HiDef video screen as the primary camera 150 to a power source. Initial power-up is enabled through a sealed switch on the side of the HiDef video screen. Actuation may then occur via proximity sensor (not shown), which may also activate or awaken the imaging system 100 from a sleep mode. The proximity sensor may also enable the display of the imaging system's 100 controls, which may appear at the bottom of the HiDef Video Screen. The display screen controls may include video/freeze-frame, f/stop (depth-of-field), ring-light, white balance, brightness, contrast, clarity, and color saturation. The Hi-Def video screen may also incorporate dual SD video card slots, which may be located on the same side of the device as the sealed power switch, behind a sealed door. The SD cards may enable recording of procedures performed by the primary camera module 150 of the imaging system 100 and/or the secondary imaging device 230. The primary camera 150, the secondary camera 230, and the HiDef video screen may communicate via Bluetooth®. The Bluetooth® module may reside within the tray 142 of the imaging system 100.

The tubular-shaped sections 110, 112, 114, 122, 126, 128, and/or 140 of the imaging system 100 may be formed from any suitable plastic or metal. Similarly, the rotatable collars 116, 118, 120, 124, and 127 of the imaging system 100 may also be formed from any suitable plastic or metal. In an exemplary embodiment, this plastic or metal may be of medical grade and/or may possess material properties to withstand the rigors of autoclave sterilization.

With continuing reference now to the lower arm 140 of the imaging system 100, the tray 142 may be mounted to an end of the lower arm 140, as shown in FIG. 1. The tray 142 may be formed with a tray surface 143 that may be used by a medical practitioner (e.g., dentist, dental hygienist, physician, surgeon, etc.) to place or temporarily store their surgical tools (e.g., dental or medical tools) during an operation or medical procedure, and/or may serve as an instrument tray. The tray 142 may be formed as a rectangular block, as shown, and may be configured and dimensioned such that a controller (not identified) may be housed within the tray 142. This controller may be powered by the power cable 106 to perform a variety of functions. The controller may include a computer processing unit to control the imaging system 100 and/or to communicate with a primary camera module 150, either wirelessly (via Bluetooth®, Wi-Fi, or similar non-wired communication) or with a wire connected between the housing of the tray 142 and the housing of the primary camera module 150. The controller may also be adapted to communicate with a remote database or filing system (e.g., dental office online portal where dentists can access patient records and/or communicate with other dentists). In an exemplary embodiment, the controller may also be configured and/or adapted to be in wireless communication with the portable display 132 detachably mounted within the display holder 130. As described, the portable display 132 may be "press-fit" into the display holder 130, as shown in FIG. 1.

In an exemplary embodiment, and in accordance with an aspect of the present disclosure, during operation of the system 100, a practitioner (e.g., dentist, doctor, etc.) may take or capture an image of the intraoral cavity or mouth etc. and a fiber optic cable talks or is in electrical communication with the controller, as described above. The system may include a CPU and/or signal processing capabilities in the controller stored in the tray unit housing 142. Then, the tray unit 142 may be configured to communication the signal (i.e., image) captured by the camera to a display screen 132. In another embodiment, the camera may wireless transmit the signal directly from the primary camera module to the display screen 132, via wireless communication, via Bluetooth®, or over a cloud computing uplink/downlink.

The tray 142 may also be formed with one or more hangers 144, as shown in FIG. 1. The hangers 144 may be formed on a side wall of the tray unit 142, as shown. Each hanger 144 may be configured and dimensioned to receive one or more tools of the medical or dental practitioner (or their assistant). For example, and in an exemplary embodiment of the present disclosure, a camera housing 154 of the primary camera module 150 may be temporarily hung or stored within the tray 142 via the hanger 144 when the camera is not needed by the practitioner or while the imaging system 100 is not being used and/or is in storage. For example, in an exemplary embodiment, the primary camera module 150 may be stored in the first hangar slot (i.e., the hanger 144 directly adjacent the module 150). The imaging system 100 may also include a 3-D scanner (not shown) for acquiring 3-D patient images, and/or a miniaturized radiographic head (not shown) for acquiring x-rays and the like. The 3-D scanner may be parked or stored in hanger position number 2, while the miniaturized radiographic head may be parked or held in hanger position number 3.

Figure 5:
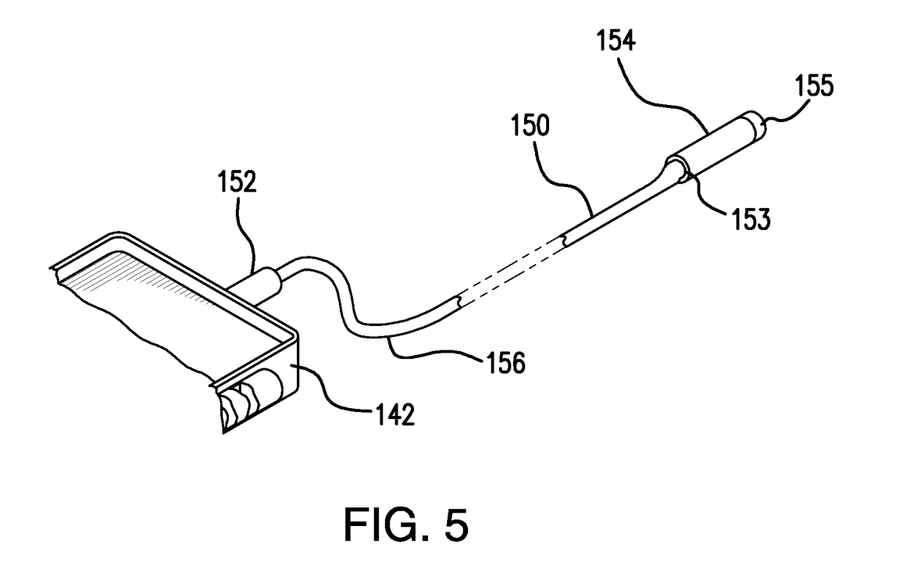
FIG. 5 illustrates an enlarged, perspective view of the primary camera module of the portable multifunctional intraoral imaging system shown in FIG. 1, in accordance with an exemplary embodiment of the present disclosure.

In an exemplary embodiment, the primary camera module 150 may include a proximal connection section 152 that may be used to mount or connect the primary camera module 150 to the tray unit 142 of the imaging system 100, as shown, for example, in additional detail in FIG. 5. The primary camera module 150 may also include a "bend-and-stay" section 156. This "bend-and-stay" section 156 may be formed with a bend-and-stay steel wire (e.g., multipurpose 304 Stainless Steel Wire or any other suitable metal wire that may permit the camera unit to "bend-and-stay"). A housing unit (not identified) may be used to house the bend-and-stay metal wiring, and may also include power cables and/or other cables to power the primary camera module 150. The housing unit may also store one or more wired connections to connect the camera of the primary camera module 150 to the controller housed within the tray unit 142. Images and/or video taken by the primary camera module 150 may be stored within computer memory (e.g., RAM, SD-cards, and the like) housed within the tray 142. The controller may be in electronic communication with the computer memory.

In an exemplary embodiment, the primary camera 155, as shown in FIG. 5, of the primary camera module 150, may be attached to the "bend-and-stay" tubing 156 that permits ease of positioning by the practitioner. There may optionally be telescoping arms with locks to facilitate the camera position. The power source may run through the bend-and-stay tubing 156 from the camera body 154 to a junction box (not identified) within the tray 142 of the imaging system 100.

This same power junction box may also serve to connect the imaging system's 100 HiDef Video Screen (e.g., portable display 132) to a continuous power source as well. As previously mentioned, the imaging system 100 may be powered via the tethered power cable 106.

In an exemplary embodiment, the imaging system's 100 primary camera 150 may include a body/lens unit sealed against water and dust penetration. The primary camera module 150 housing may also be hermetically sealed. The primary camera body/lens unit may be approximately 40 mm (width)-X-40 mm (height)-X-80 mm (length). The primary camera 150 may utilize an approximately 24.0 mm×16.0 mm, 24-26-megapixel, APS-C-sized, CMOS sensor that may incorporate a 5-axis stabilization system and an ultrasonic vibration cleaning system. The primary camera sensor may have a non-detachable low pass filter and may also utilize RGB primary color filters. The primary camera 150 CMOS sensor may provide for Auto-Focus with a detection range of approximately 90% vertical and 90% horizontal of the field-of-view. The primary camera 150 CMOS sensor may operate on an automatic ISO with a range of approximately 160 to 25,600 and may utilize automatic white balance featuring ambiance priority or white priority and is further adjustable for tungsten and fluorescent lighting; light is metered via a center-weighted average. The primary camera 150 CMOS sensor may provide for continuous auto-focus as well as freeze-frame (single-frame) autofocus with continuous subject tracking-once a focus-point is selected via the HiDef Video Screen, the system may automatically re-center the image on the HiDef Video Screen (e.g., portable display 132) to represent the focus point; utilizing pinch and spread hand motions, the practitioner 190 (e.g., the dentist, his assistant, or other suitable medical practitioner) zooms the focus point to the appropriate scale per procedure. The primary camera 150 body may be equipped with an electronic shutter for both single frame and/or video imaging. The primary camera may record in 4K Ultra High-Definition video.

The primary camera 150 lens may be set at a fixed 41°/65° field-of-view (approximately 50 mm-35 mm lens equivalent in 35 mm format). The lens may provide for f-stops from 5.6-28, providing for adequate depth-of-field and macro-level detail for all dental procedures. The primary camera 150 lens may incorporate an LED ring-light to enhance visualization.

Figure 2:
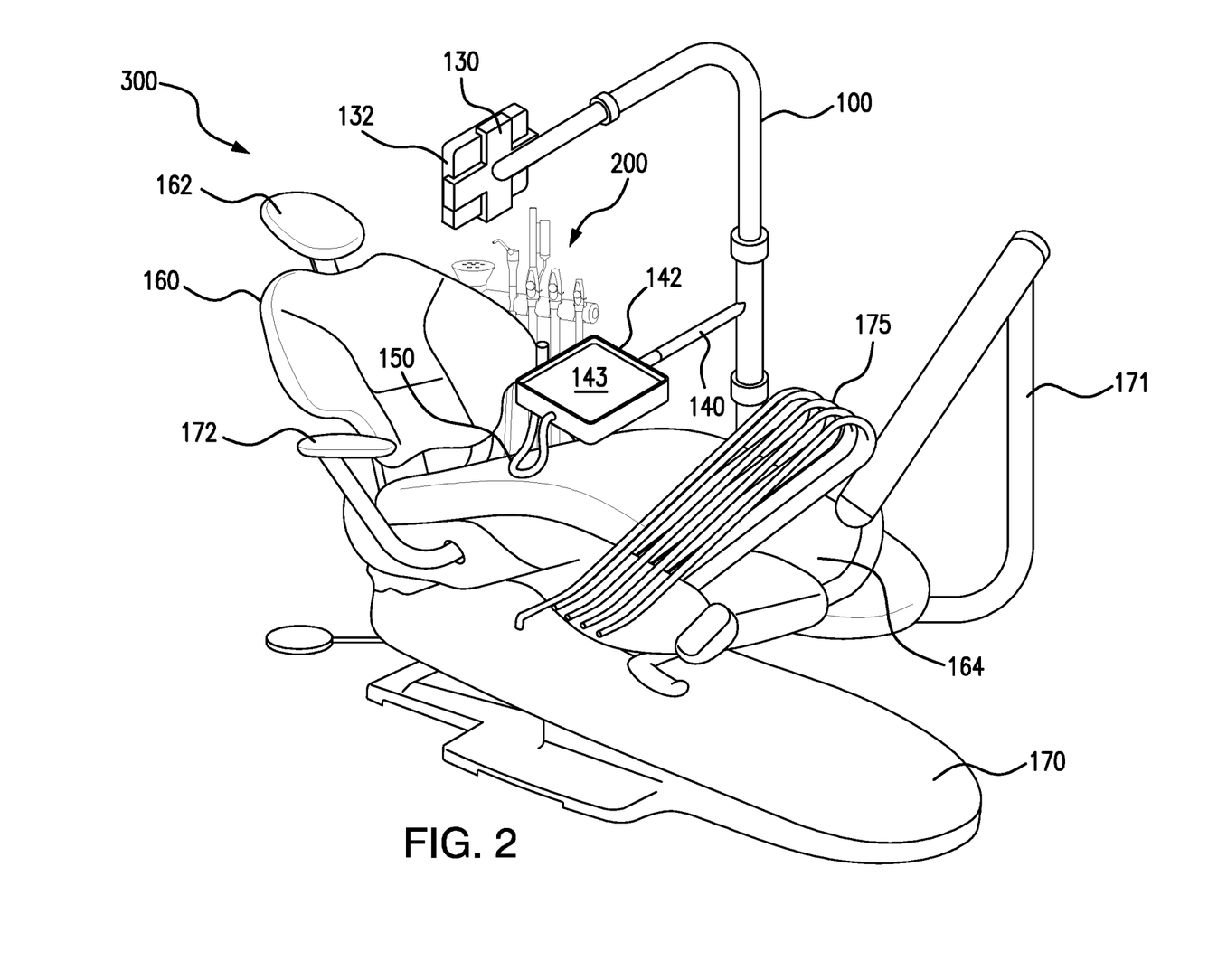
FIG. 2 illustrates a perspective view of a dental operating theater, including the portable multifunctional intraoral imaging system depicted in FIG. 1, in accordance with an exemplary embodiment of the present disclosure.
Figure 3A:
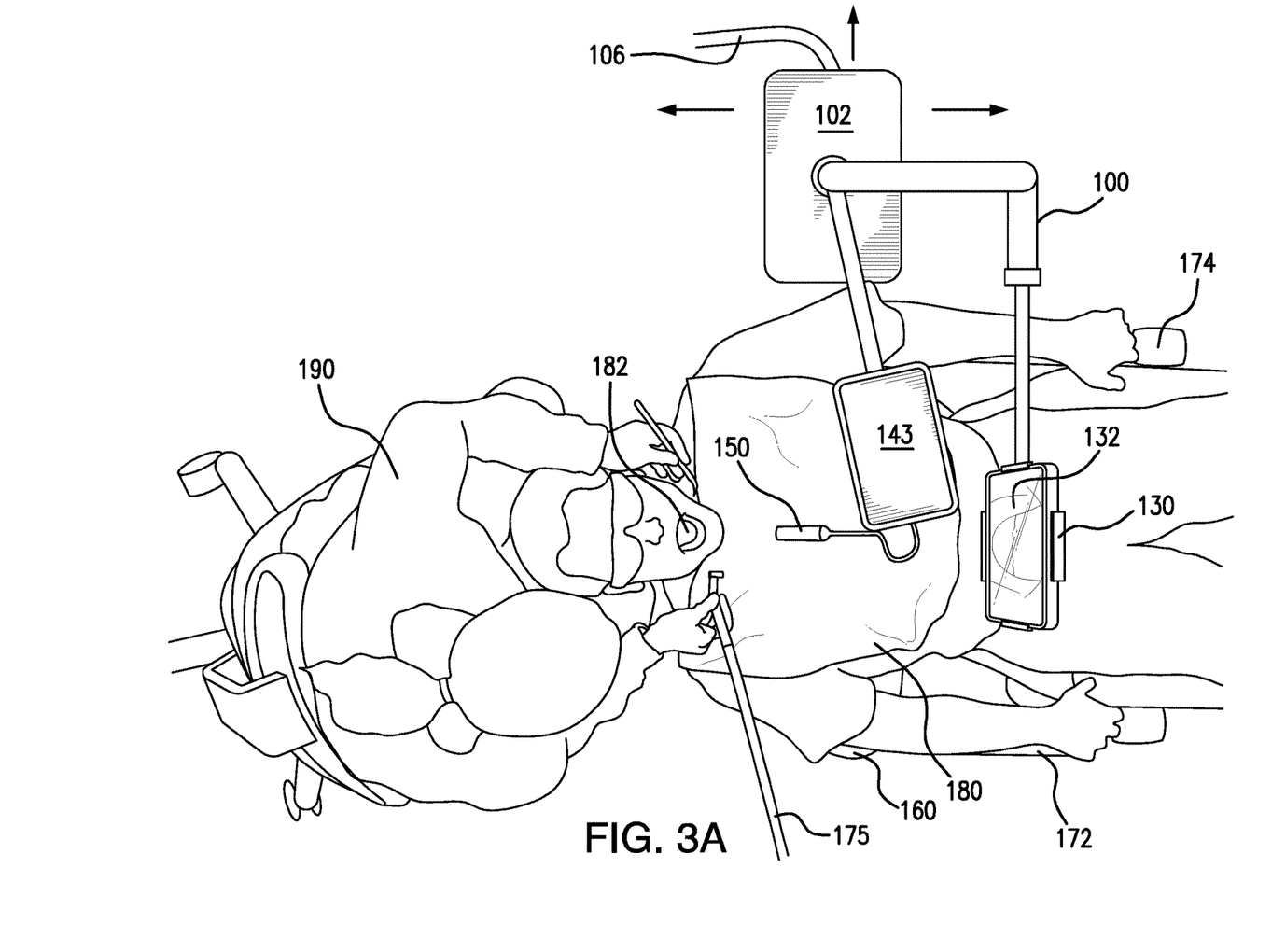
FIG. 3A illustrates a top view of the dental operating theater of FIG. 2 with a patient and a medical practitioner (i.e., dentist), including the portable multifunctional intraoral imaging system depicted in FIG. 1 being utilized by the medical practitioner (i.e., dentist) to perform a medical/dental procedure on the patient, in accordance with an exemplary embodiment of the present disclosure.

FIG. 2 illustrates a perspective view of a dental operating theater 300, including the portable multifunctional intraoral imaging system 100 depicted in FIG. 1, in accordance with an exemplary embodiment of the present disclosure. As shown in FIG. 2, the dental operating theater 300 includes the imaging system 100, as described herein, and a secondary assistant-side delivery unit 200. The dental operating theater also includes a patient's chair 160. The patient's chair 160 may be a suitable dental chair having the appropriate electrical, plumbing, and/or network connection required by the medical procedure to be performed by the practitioner. The patient's chair 160, or dental chair 160, may include a headrest 162, a footrest 164, a base unit 170, and opposed armrests 172 and 174 (FIG. 3A). In the exemplary embodiment shown in FIG. 2, the dental chair 160 may also include a Dentist-side delivery system or armamentarium 175 (e.g., dentist's drills, and other tools). The Dentist-side delivery system or armamentarium 175 may be rotatably mounted at the footrest end 164 of the dental chair 160 such that the Dentist-side delivery system or armamentarium 175 may be rotated about the Z-axis to permit the Dentist-side delivery system or armamentarium 175 to be brought closer to the dentist during a procedure. In an exemplary embodiment, a boom 171 may also be secured and/or mounted to the dental chair 160. Boom 171 may be part of the boom that permits positioning of the Dentist-side delivery system; it may be mounted to the base 170 of the dental patient chair. It can be appreciated that other delivery system(s) or armamentarium(s), other dentist-side or dentist-assistant-side may be mounted to the dental chair 160 or otherwise made available in the dental operating theater 300.

As shown in FIG. 2, the imaging system 100 of FIG. 1, is movable and portable in the dental operating theater 300 such that the imaging system 100 is not secured or affixed or mounted in any way to the dental chair 160. The imaging system 100 may be movable along the X- or Y-axes on the floor of the dental operating theater 300. As shown in FIG. 2., when the imaging system 100 is inactive or not being used by the practitioner, the primary camera module 150 is temporarily stored or hung on the hanger 144 of the tray 142. While the portable display 132 is releasably mounted within the display holder 130, it can be appreciated that the portable display 132 is portable and may be taken out by the practitioner and transported to areas not in the dental operating theater 300 (e.g., for consulting with other dental practitioners in other dental operating theaters, or other parts of a medical practice).

Figure 3B:
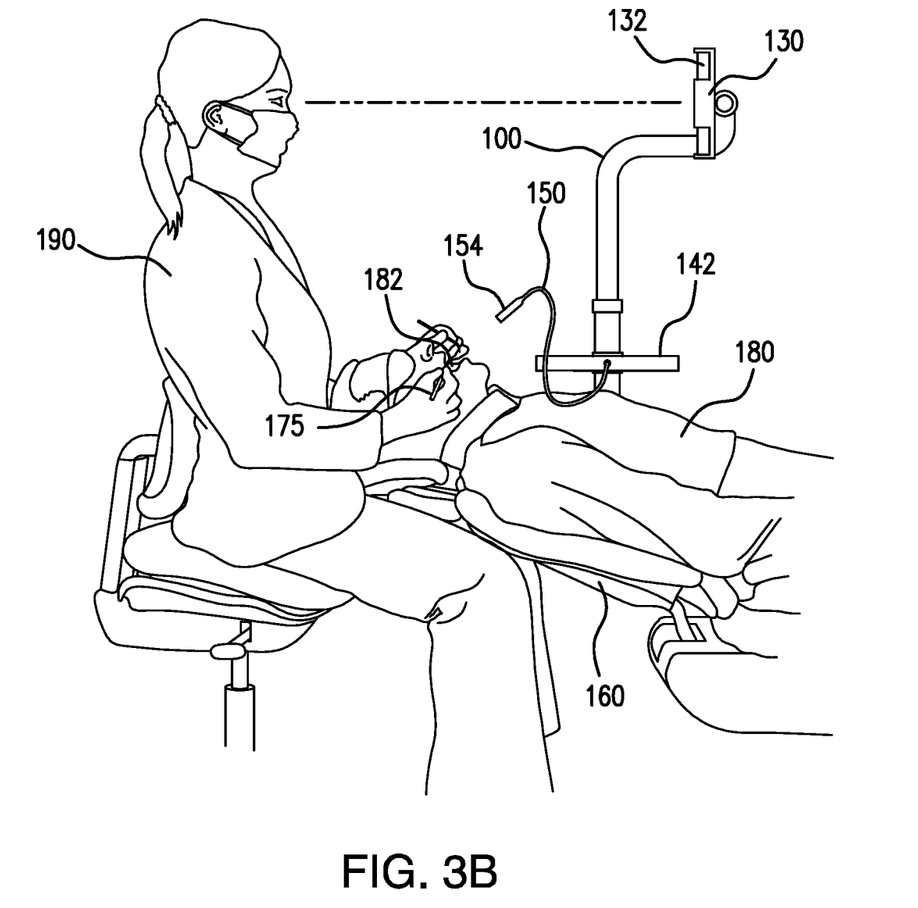
FIG. 3B illustrates a side view of the dental operating theater of FIG. 2 with a patient and a medical practitioner (e.g., dentist), including the portable multifunctional intraoral imaging system depicted in FIG. 1 being utilized by the medical practitioner (e.g., dentist) to perform a medical/dental procedure on the patient, and further illustrating an assistant-side delivery unit mounted to the patient's chair, in accordance with an exemplary embodiment of the present disclosure.

With initial reference to FIGS. 3A and 3B, the portable imaging system 100 is shown when employed by a practitioner 190 during an operation or medical/dental procedure. For example, FIG. 3A illustrates a top view of the dental operating theater 300 of FIG. 2 with a patient 180, seated within the dental chair 160, and a medical practitioner 190 (i.e., dentist), including the portable multifunctional intraoral imaging system 100 depicted in FIG. 1 being used by the medical practitioner (i.e., dentist) to perform a medical/dental procedure on the patient. During the procedure, the camera of the primary camera module 150 may be positioned such that the camera is 18-36 inches away from inside the mouth 182 of the patient 180 (e.g., intraoral cavity 182 where the teeth are to be examined/imaged). An advantage of this 18-36 inch spacing is, given the resolution capability of the primary camera module 150, the camera head 154 may disposed 18-36 inches from the oral cavity. Given the primary camera module's 150 resolving capability and its lens' depth of field, the primary camera module 150 can provide detailed imaging far enough from the mouth 182 of the patient 180 so as not to become fogged by the patient 180 or sprayed by the dental high speed drill (which utilizes an air-water spray to cool the cutting surface of the dental drill bit; similarly, the low speed, high torque drill utilized by implant surgeons). This is an advantage of the imaging system 100 of the present disclosure over known commercially available devices.

As depicted on the screen of the portable display 132, during imaging and/or the surgical procedure, the patient's intraoral image may be relayed to be viewed by the practitioner 190 by looking straight ahead into the portable display 132 instead of down into the patient's mouth 182. In an exemplary embodiment, the portable display 132 of the imaging system 100 may be positioned in the dental operating theater 300 such that a plane of the portable display 132 is aligned with a plane of the patient's navel or a plane of the patient's waist (as shown). During an exemplary operation of the imaging system 100, the lower arm 140 (FIG. 2) may be rotatably adjusted by the practitioner (or their assistant) to move the tray unit 142 such that the primary camera module may be positioned or moved along the X-Y plane of the dental operating theater 300. Moreover, the practitioner, during the procedure, may also reconfigure or adjust the bend-and-stay wire 156 of the primary camera module 150 to the practitioner's satisfaction such that the camera suitably captures the intraoral cavity 182 of the patient 180. FIG. 3B provides a side view of the dental operating theater 300 of FIG. 2 with the patient 180 and the medical practitioner 190 (e.g., a dentist 190), including the portable multifunctional intraoral imaging system 100 depicted in FIG. 1. As shown in FIG. 3B, although the camera must be pointed down at an angle to match the patient's intraoral cavity 182, the display 132 may be positioned straight at the eye level of the medical practitioner 190 such that the practitioner 190 (e.g., the dentist 190) may look straight at the portable display 132 without bending the practitioner's 190 neck up or down to avoid any strain. Additionally, as shown in FIG. 3B, the practitioner's 190 hands are resting below the face of the patient 180 such that the practitioner is in a more relaxed stance thereby reducing strain on the practitioner's hands, body, and/or lower back during the procedure. It is a benefit of the imaging system 100 that, during use of the system 100, a practitioner 190 (e.g., a dentist) can avoid looking down into a patient's mouth and instead look straight across at the adjustable (e.g., rotatable) portable display 132. Moreover, the practitioner 190 may adjust the height of the portable display 132 and/or the tray 142 by utilizing the height adjustment features described and illustrated with respect to FIG. 1. The practitioner 190 may also rotate the portable display 132 using the display holder 130, also described and illustrated with respect to FIG. 1.

Figure 4:
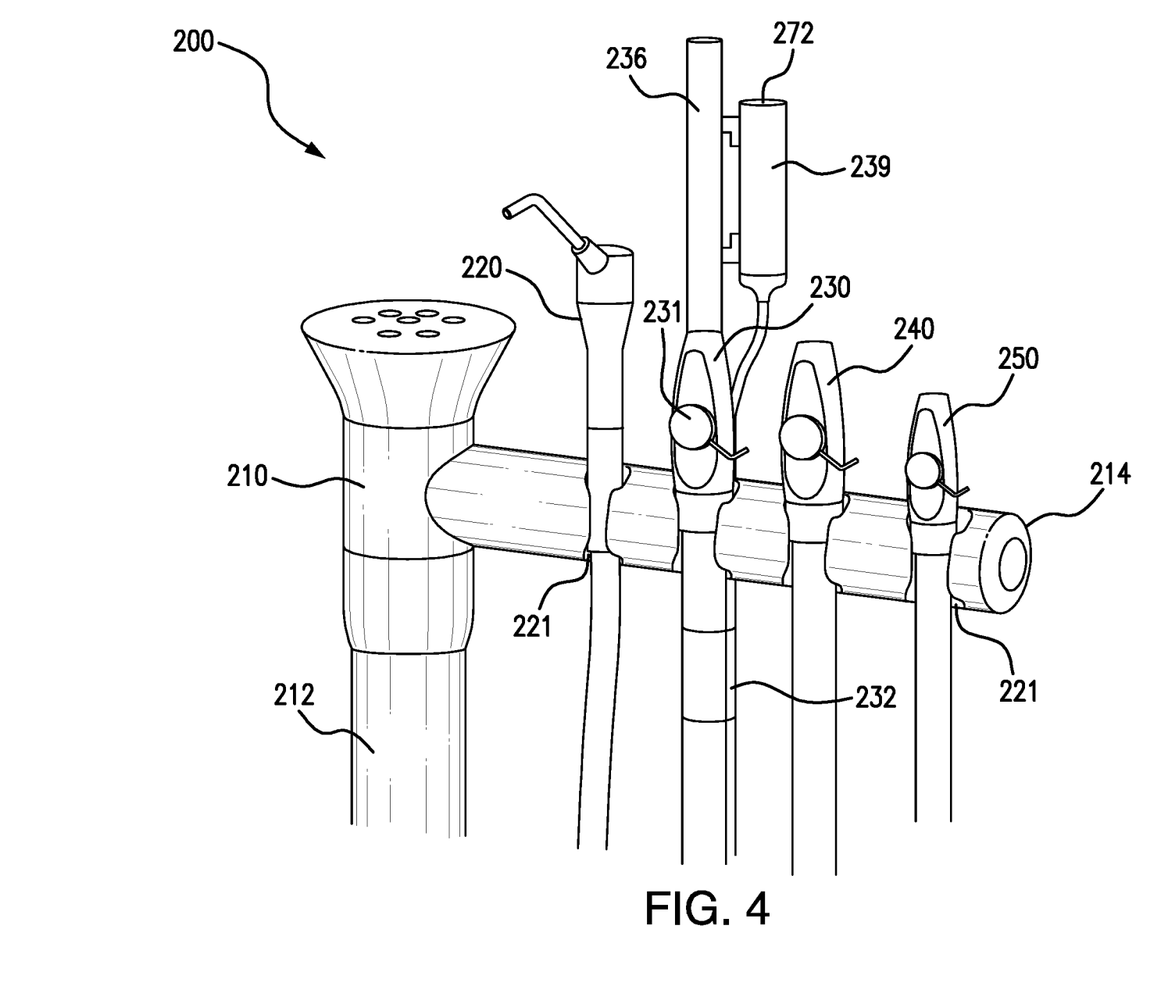
FIG. 4 illustrates an enlarged, perspective view of the assistant-side delivery unit of FIG. 2, and depicting a three-way syringe, a secondary camera module (e.g., an extraoral camera within a sealed case, clamped to an assistant's high-volume suction tube); a secondary high-volume suction tube; and a saliva ejector, in accordance with an exemplary embodiment of the present disclosure.

With reference now to FIG. 4, therein is depicted an enlarged, perspective view of the assistant-side delivery unit 200 of FIG. 2. In an exemplary embodiment, the assistant-side delivery unit 200 may include multiple sub-units. For example, and as shown in FIG. 2, the delivery unit 200 may include a three-way syringe 220, a secondary camera module with a high-volume suction tube 230 (e.g., an extraoral camera within a sealed case, clamped to an assistant's high-volume suction tube); a secondary high-volume suction tube 240; and a saliva ejector 250. The three-way syringe 220, the secondary camera module with the high-volume suction tube 230, the secondary high-volume suction tube 240; and the saliva ejector 250 may be hand-held and may be operated by the practitioner's 190 assistant under real-time guidance or instructions provided by the practitioner 190 (e.g., dentist) to the assistant. In an exemplary embodiment, the assistant-side delivery unit 200 may be mounted or otherwise secured to the patient's chair 160 of the dental operating theater 300. The assistant-side delivery unit 200 is not mounted or connected in any way to the imaging system 100; preferably, they are separate components. The assistant-side delivery unit 200 is a fixed unit, while the imaging system 100 is a portable or moveable unit, as taught herein. The assistant-side delivery unit 200 may be formed as an L-shaped bracket and may include a mounting arm 210 and a transverse arm 214. The mounting arm 210 of the delivery unit 200 may be connected, for example, to the dental-assistant-side of a patient's chair via the section 212. In an exemplary embodiment, the assistant-side delivery unit 200 may include internal structure and/or components to provide necessary electrical power, water, suction means to permit the practitioner 190 (e.g., dental assistant) to adequately use the three-way syringe 220, the secondary camera module 230; the high-volume suction tube 240; and the saliva ejector 250. The transverse arm 214 of the assistant-side delivery unit 200 may also include one or more recesses or hangers 221 to store or hold the three-way syringe 220, the secondary camera module 230; the high-volume suction tube 240; and the saliva ejector 250 when not in use. Moreover, and according to an exemplary embodiment taught herein, the secondary camera module 230 may also include a separate power cable 232 to supply power to a camera housed within the secondary camera module housing unit 239. As shown in FIG. 4, the assistant-side delivery unit 200 may include a secondary camera module with a high-volume suction tube 230 (e.g., an extraoral camera within a sealed case, clamped to an assistant's high-volume suction tube) to allow a practitioner or a practitioner's assistant to provide a secondary imaging source in the dental operating theater 300. For example, when the primary camera module 150 is set by the practitioner 190 (e.g., the dentist 190) to view an intraoral cavity 182 of the patient 180, the practitioner 190 (e.g., dentist) may instruct the dental assistant to provide additional imaging by using the hand-held secondary camera module 230 to look at a different angle or view of the intraoral cavity 182 other than the one the practitioner 190 (e.g., dentist 190) is seeing using the primary camera module 150. The image captured by the secondary camera module 230 may be wirelessly transmitted to be displayed on the portable display 132 (e.g., practitioner's tablet PC). In an exemplary embodiment, the image provided by the primary camera module 150 may be adjacent or positioned next to the image provided by the secondary camera module 230 within the display screen of the portable display 132. In an exemplary embodiment, the controller, housed within the tray 142 of the imaging system 100, may be the intermediary to transfer, receive and/or send images or video from the secondary camera module to the portable display 132, for example, via Bluetooth® or Wi-Fi or other wireless network connection. Moreover, the portable display 132 may be configured to be interactive (e.g., touch display) such that the practitioner 190 (e.g., dentist) or their assistant may pinch-and-zoom the one or more images and/or video being captured by the primary or secondary camera modules 150 and 230.

Figure 6:
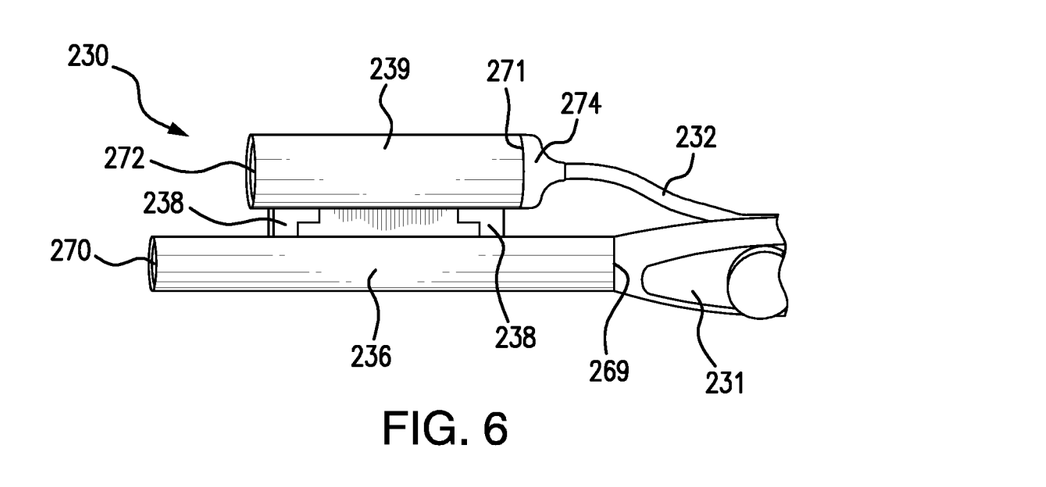
FIG. 6 illustrates an enlarged, perspective view of the secondary camera module of the assistant-side delivery unit of FIGS. 2 and 4, in accordance with an exemplary embodiment of the present disclosure.

FIGS. 5 and 6 depict the detailed structure of the primary and secondary camera modules 150 and 230, respectively. For example, FIG. 5 illustrates an enlarged, perspective view of the primary camera module 150 of the portable multifunctional intraoral imaging system 100 shown in FIG. 1. FIG. 6 illustrates an enlarged, perspective view of the secondary camera module 230 of the assistant-side delivery unit 200 of FIGS. 2 and 4, in accordance with an exemplary embodiment of the present disclosure. According to an exemplary embodiment, with reference to FIG. 6, the secondary camera module 230, may include a secondary camera housed within a housing 239 coupled to a high-volume suction tube 236 (e.g., an extraoral camera 272 within a sealed case 239, clamped to an assistant's high-volume suction tube 236). The high-volume suction tube 236 may include a distal end 270 that may be used to suck matter from a patient's mouth during a procedure (e.g., discarded tissue, blood, teeth fragments, water, or other liquids, etc.)

In another embodiment, the camera may wireless transmit the signal directly from the secondary camera module to the display screen 132, via wireless communication, via Bluetooth®, or over a cloud computing uplink/downlink.

The secondary camera housing 239 may be mounted or otherwise attached to the high-volume suction tube 236 via one or more mounting brackets 238, as shown in FIG. 6. The secondary camera housing 239, the high-volume suction tube 236, and the mounting brackets 238 may be formed integrally as one piece or be separate pieces fused or connected together. In an exemplary embodiment, the secondary camera housing 239, the high-volume suction tube 236, and the mounting brackets 238 may be formed from a material (e.g., metal) that can endure autoclave sterilization or otherwise capable of being heated/sterilized so the assembly may be reused in future procedures. However, in order to permit such sterilization to occur the secondary camera module must be disconnected via the power adapter 274 at a proximal end 271 of the secondary camera housing 239. The adapter 274 may allow the secondary camera housing 239 to be snap-fitted or screwed on. The secondary camera within the secondary camera housing 239 may be accessed from the rear, proximal end 271, where a watertight (i.e., rubber) closure that contains the power adapter 274 may be secured in place, thus sealing the secondary camera body 239 from liquid, dust, and biologic contamination. When the secondary camera module is disconnected for sanitization purposes, the secondary camera may be secured to the adapted 274 and the secondary camera power supply cable 232 such that only the housing section 239, together with the mounting brackets 238 and the suction tube 236 are disconnected from the device 230. The suction tube 236 is a press-fit and may be snapped on or off at proximal end 269, as shown.

In an exemplary embodiment, the secondary camera module 230 may be mounted in a tube that may be permanently attached to a dental high-volume suction evacuator (HVE). The purpose of the secondary camera may be to provide a different, lateral perspective of the operating area to the dentist without altering the position of the primary camera. The secondary camera tube 239 and the high-volume suction evacuator 236 may be fabricated of a sterilizable metal (stainless steel). The secondary camera tube 239 may be seated approximately 5-10 mm above the high-volume evacuator tube 236 and may be approximately two-thirds its size. The front or distal end 272 of the secondary camera tube 239 may also be sealed with a scientific-grade glass 0-diopter lens that permits visualization of the working area (lateral perspective) by the secondary camera.

The secondary camera may be housed within an approximately 20 mm diameter X 80 mm long tube (e.g., tube 239) incorporating a lens set 272 at one end and a power input 232 at the other. The secondary camera may utilize a sensor of approximately 15 mp with an electronic shutter and may be stabilized against vibration and sudden movement. The sensor may provide continuous autofocus around a central, discriminating focus area that is continuously tracking a subject. The lens set may produce a 28-to-35 mm (equivalent) field of view at a constant f22. The secondary camera may be inserted within the tube atop the HVE, may be secured intimately with a machined fit, and may be sealed in place by securing the watertight (rubber) power source 274 at the rear, proximal end 271 of the tube 239.

The imaging system 100 may also require data processing or software functionality and capability. The software may be stored in a digital storage medium (e.g., RAM) housed within the tray unit 142 of the imaging system 100. The software may also be uploaded to a cloud computing storage device or a central server and may be accessed via the controller, as taught herein, using either a wireless or wired Internet connection, or some other similar medium of digital data transfer. The imaging system 100, and/or the secondary camera module, may require any of the following software requirements:

Software may accommodate touchscreen interface for control of all camera functions, (i.e., focus point; ASA/ISO; f-Stop/Depth of Field; Zoom/Macro functions—Pinch/Spread; Brightness/Exposure; Contrast; Clarity; White Balance; Color Saturation; etc.);

Data processing or software may permit for all camera functions—video, single frame, digital scan, etc.;

Data processing or software may provide for sensor to activate adjustments menu upon approaching hand;

Data processing or software may allow for multi-field focus points (i.e., ±75-90 points of focus covering 90% vertical and horizontal dimension of the imaging system HiDef screen);

Data processing or software may allow for selection of focus point from wide angle view→centering of selected focus point→enlarging via Zoom-Macro/pinch-spread function;

Data processing or software may be capable of accurate digital enhancement of video imaging;

Data processing or software may provide for automatic focus tracking;

Data processing or software may distinguish between instruments, dental handpiece and focus point;

Data processing or software may accommodate Bluetooth® connectivity between the primary and secondary cameras and the HiDef touch/viewscreen;

Data processing or software may enable lab communication for 3-D digital impression/scan and/or interface with in-office milling device;

Data processing or software may accommodate for split-screen functionality (i.e., primary and secondary camera feeds; radiographs/CBCT);

Data processing or software may interface with patient computerized records (i.e., CBCT and/or radiographs);

Data processing or software may interface camera functions with patient charts for storage of data;

Data processing or software may provide and allow for manipulation of CBCT and/or radiographic imaging to assist in diagnosis and treatment;

Data processing or software may have the capability to translate patient (e.g., intraoral treatment position to CBCT/radiographs for an overlay function (principally for implant guidance, restorative parallelism, etc.));

Data processing or software may essentially function as a real-time, virtual surgical, prosthodontic stent; and Data processing or software may interface with a micro-radiographic head to allow endodontic procedures facilitated via real-time radiographic imaging projected to HiDef touch/videoscreen and digital snapshots (e.g., pre-tx, exact length, master cone fit, final fill).

Apart from the requirements above, it can be appreciated that other examples of such software libraries and/or services may be used by the imaging system 100.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

I claim:
1. An imaging and display system, comprising:
a base;
a pole connected to and extending generally upward from the base;
a tray unit having a distal end and a proximal end and connected to the pole at its proximal end and extending generally outward with respect to an axis of the pole, the distal end of the tray unit connected to a camera;

an upper arm having a distal end and a proximal end, the proximal end of the upper arm connected to the pole and extending in a generally upward direction with respect to the axis of the pole, the distal end of the upper arm including a generally transverse direction with respect to the axis of the pole; and a display connected to the distal end of the upper arm.

2. The imaging and display system of claim 1, wherein the camera is connected to the tray unit using a bend-and-stay mechanism.

3. The imaging and display system of claim 1, wherein the upper arm is connected to the pole by way of a rotatable collar to allow the upper arm to rotate with respect to the pole.

4. The imaging and display system of claim 1, wherein the display is connected to the distal end of the upper arm by way of a rotatable collar to allow the display to rotate with respect to the distal end of the upper arm.

5. The imaging and display system of claim 1, wherein the pole is generally tubular.

6. The imaging and display system of claim 1, wherein the tray unit is connected to the pole by way of an arm and a rotatable collar to allow rotation of the tray unit.

7. The imaging and display system of claim 1, wherein the pole is adjustable in height.

8. The imaging and display system of claim 7, wherein the pole includes a telescoping mechanism to allow for adjustment in height.

9. The imaging and display system of claim 8, wherein the pole further comprises a plurality of telescoping members interconnected using rotatable collars.

10. The imaging and display system of claim 1, further comprising a plurality of wheels connected to the base.

11. The imaging and display system of claim 1, further comprising a controller and a wireless communications interface operable to wirelessly transmit image information obtained by the camera.

12. The imaging and display system of claim 1, further comprising a foot operated controller operable to control the camera, the display, or a setting of the camera or the display.

13. An imaging and display system operable to provide intraoral imaging and display of intraoral images, the system comprising:

a base having a plurality of wheels connected thereto;

a generally tubular shaped pole connected to and extending generally upward from the base, the pole being adjustable in height;

a tray unit having a distal end and a proximal end and connected to the pole at its proximal end and extending generally outward with respect to an axis of the pole, the distal end of the tray unit connected to a camera, the camera being operable to be positioned in an intraoral region of a patient;

an upper arm having a distal end and a proximal end, the proximal end of the upper arm connected to the pole and extending in a generally upward direction with respect to the axis of the pole, the distal end of the upper arm including a generally transverse direction with respect to the axis of the pole; and a display connected to the distal end of the upper arm, the display operable to display images of the intraoral region of the patient.

14. The imaging and display system of claim 13, wherein the camera is connected to the tray unit using a bend-and-stay mechanism.

15. The imaging and display system of claim 13, wherein the upper arm is connected to the pole by way of a rotatable collar to allow the upper arm to rotate with respect to the pole.

16. The imaging and display system of claim 13, wherein the display is connected to the distal end of the upper arm by way of a rotatable collar to allow the display to rotate with respect to the distal end of the upper arm.

17. The imaging and display system of claim 13, wherein the tray unit is connected to the pole by way of an arm and a rotatable collar to allow rotation of the tray unit.

18. The imaging and display system of claim 13, wherein the pole includes a telescoping mechanism having a plurality of telescoping members interconnected using rotatable collars to allow for adjustment in height.

19. The imaging and display system of claim 13, further comprising a controller and a wireless communications interface operable to wirelessly transmit image information obtained by the camera.

20. The imaging and display system of claim 13, further comprising a foot operated controller operable to control the camera, the display, or a setting of the camera or the display.

* * * * *